United States Patent [19]

Hebrank

[11] Patent Number: 4,914,672
[45] Date of Patent: Apr. 3, 1990

[54] METHOD AND APPARATUS OF DISTINGUISHING BETWEEN LIVE AND DEAD POULTRY EGGS

[75] Inventor: John H. Hebrank, Durham, N.C.

[73] Assignee: Embrex, Inc., Durham, N.C.

[21] Appl. No.: 219,205

[22] Filed: Jul. 14, 1988

[51] Int. Cl.⁴ .................. G01K 13/06; G01K 7/02; G01K 7/22; G01J 5/00

[52] U.S. Cl. .................. 374/124; 250/342; 209/510; 209/511; 209/577; 209/643; 374/134; 374/166; 374/178; 374/179; 374/183

[58] Field of Search .................. 374/134, 29, 45, 124, 374/166, 178, 179, 183; 250/342, 358.1; 209/510, 511, 552, 576, 577, 643

[56] References Cited

U.S. PATENT DOCUMENTS

| | | | |
|---|---|---|---|
| 2,118,794 | 5/1938 | King | 356/36 |
| 2,823,800 | 2/1958 | Bliss | 209/511 |
| 3,373,869 | 3/1968 | Burson, Jr. | 209/3.1 |
| 3,395,793 | 8/1968 | Thompson et al. | 209/3.1 |
| 3,433,052 | 3/1969 | Maley | 374/5 |
| 3,463,007 | 8/1969 | Jones et al. | 374/24 |
| 3,492,073 | 1/1970 | Michael | 356/53 |
| 3,740,144 | 6/1973 | Walker | 356/53 |
| 3,747,755 | 7/1973 | Senturia et al. | 209/577 |
| 4,025,422 | 5/1977 | Malvick et al. | 209/577 |
| 4,161,366 | 7/1979 | Bol et al. | 356/56 |
| 4,203,522 | 5/1980 | Fraenkel et al. | 209/577 |
| 4,225,242 | 9/1980 | Lane | 356/407 |
| 4,262,806 | 4/1981 | Drabs | 209/577 |
| 4,420,265 | 12/1983 | Everest et al. | 374/124 |
| 4,671,652 | 6/1987 | van Asselt et al. | 356/66 |
| 4,681,063 | 7/1987 | Hebrank | 119/1 |
| 4,788,427 | 11/1988 | LeRoy | 374/124 |

FOREIGN PATENT DOCUMENTS

| | | | |
|---|---|---|---|
| 64842 | 11/1982 | European Pat. Off. | 209/577 |
| 60-79249 | 5/1985 | Japan | 209/511 |
| 657800 | 4/1979 | U.S.S.R. | 209/577 |
| 969581 | 9/1964 | United Kingdom | 209/577 |
| 1274449 | 5/1972 | United Kingdom | 209/577 |
| 2188727 | 10/1987 | United Kingdom | 209/577 |

Primary Examiner—William A. Cuchlinski, Jr.
Assistant Examiner—Diego F. F. Gutierrez
Attorney, Agent, or Firm—Bell, Seltzer, Park & Gibson

[57] ABSTRACT

The invention is a method of distinguishing between live and dead poultry eggs. The method comprises monitoring the individual temperatures of the selected group of eggs and then using the monitored individual egg temperatures to determine a comparative egg temperature for the selected group. The difference between each individual egg temperature and the comparative egg temperature of the selected group is determined, and dead eggs are identified on the basis of the difference between their monitored individual temperatures and the comparative egg temperature of the selected group.

21 Claims, 3 Drawing Sheets

METHOD AND APPARATUS OF DISTINGUISHING BETWEEN LIVE AND DEAD POULTRY EGGS

FIELD OF THE INVENTION

The present invention relates to methods for distinguishing between live and dead poultry eggs, and in particular relates to a method of distinguishing between such eggs by monitoring the temperature of both types of eggs.

BACKGROUND OF THE INVENTION

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with poultry eggs, although egg shells appear opaque under most lighting conditions, they are in reality somewhat translucent, and when placed in front of a direct light, such as a candle or light bulb, the contents of the egg can be observed to a certain extent.

In most such practices, the purpose of inspecting eggs, particularly "table eggs" intended for human consumption, is to identify and then segregate those eggs which have a significant quantity of blood present, such eggs themselves sometimes being referred to as "bloods" or "blood eggs." These eggs are less than desirable from a consumer standpoint, making removal of them from any given group of eggs economically desirable.

Eggs which are to be hatched to live poultry also may be candled midway through embryonic development or later to identify infertile ("clear") eggs and remove them from incubation to thereby increase available incubator space. Such inspection and removal is particularly useful in turkey hatcheries. Candlers also attempt to identify and remove "rotten" and other dead eggs on the basis of their internal color. Such techniques are difficult and unreliable, however, so that many rotten eggs are inadvertently returned to incubation.

As stated above, early techniques for identifying such eggs comprised simply inspecting the egg in front of a candle and discriminating on the basis of the appearance of the contents. Later inspection techniques used artificial light sources, and in recent years, spectrographic techniques have been developed which irradiate eggs with particular frequencies of light which are sensitive to the presence of one or more of the characteristic components of blood (e.g. hemoglobin) to make a more accurate determination of whether or not the contents of the egg are indeed filled with blood or whether some other factor is interfering with the egg's appearance or quality.

Still other techniques inspect table eggs for the purpose of determining whether or not they are cracked. These techniques also use light sources and detectors because cracked eggs will often transmit more incident light towards a detector than will intact ones.

Recently, however, there have developed other reasons for distinguishing between eggs. One of these reasons is the advancements in techniques for treating poultry embryos with medications, nutrients, hormones or other beneficial substances while the embryos are still in the egg. Such techniques are quite advantageous compared to treatment of newly born chicks which often must be medicated, for example, by being hand inoculated one by one.

In embryo treatment techniques, the purpose of discrimination between eggs is to determine whether or not the eggs are alive or dead and whether they should consequently be treated with the particular vaccine, nutrient, hormone or other material under consideration. Accordingly, the decision of whether or not to treat the egg involves greater expense than simply the cost of the egg, including the cost of the dosage of the injected material, the cost of operating any given injection system and the cost of further incubation. Additionally, infertile or early dead eggs foster bacterial growth and thus are frequently infected. An embryo injection system which penetrates an infected egg risks contaminating live eggs which are subsequently injected by the system.

Finally, although the typical tests for appearance and blood can discriminate to some extent between fertile and infertile eggs, there are no reliable automatic methods for distinguishing between live and dead eggs. Therefore, the embryonic treatment industry is in economic need of a highly reliable method of discrimination of live eggs from dead ones and particularly for the detection of infected or rotten eggs.

Of course, any technique for discriminating between live and dead eggs must be either noninvasive, or so minimally invasive, that the live eggs will not be harmed by the discrimination technique.

Accordingly, it is an object of the present invention to provide a noninvasive method of, and apparatus for, distinguishing between live and dead poultry eggs on the basis of their individual monitored temperatures.

SUMMARY OF THE INVENTION

The present invention comprises a method and apparatus for distinguishing between live and dead poultry eggs. The method comprises monitoring the individual temperatures of a selected group of eggs and using the monitored individual egg temperatures to determine a comparative egg temperature for the selected group of eggs. Dead eggs are identified on the basis of the difference between their monitored individual temperatures and the comparative egg temperature of the selected group. The apparatus of the presently preferred embodiment of the invention includes an infrared radiation sensor, means for moving fixed arrays of eggs to predetermined aligned positions with respect to the infrared sensor, means for recording the infrared radiation emitted by each egg, and means for calculating a comparative temperature from the individual temperatures in the fixed array.

The invention is premised on the discovery that regardless of thermal surroundings, dead eggs tend to be cooler than live eggs under those same conditions. Similarly, dead eggs tend to cool more rapidly than live ones. Finally, because thermal surroundings and thermal history affect the absolute temperatures of both live and dead eggs, measurement of one egg's individual temperature or cooling rate, standing alone, does not provide sufficient information to determine whether the egg is live or dead.

The foregoing and other objects, advantages and features of the invention, and the manner in which the same are accomplished will become more readily apparent upon consideration of the following detailed description of the invention taken in conjunction with the accompanying drawings, which illustrate preferred and exemplary embodiments, and wherein:

BRIEF DESCRIPTION OF THE DRAWINGS

FIG. 7 is a partial cross-sectional view of a standard egg flat used in accordance with the present invention and FIG. 8 is a view of an individual egg in contact with a temperature sensor.

DETAILED DESCRIPTION

The invention comprises a method of distinguishing between live and dead eggs. As a first step, the method comprises monitoring the individual temperatures of a selected group of eggs. In the preferred embodiment of the invention, the step of monitoring the individual temperatures comprises monitoring the infrared radiation emitted from the individual eggs as measured at the non-air cell end of the eggs in the selected group. Because the air in the air cell portion of the egg acts as an insulator, temperatures monitored from the non-air end tend to more accurately and precisely reflect the state of the egg.

Temperature can also be measured at the side of the egg, although this can be mechanically less simple for trayed eggs. Furthermore, relative temperature between the bottom and side of eggs could also be used, if desired.

As used herein, the designation "infrared radiation" refers to electromagnetic radiation having a wavelength of between about 2.5 and about 50 microns or expressed differently, that having a frequency of between about 200 and about 4000 inverse centimeters $cm^{-1}$ or "wave numbers"). As understood by those familiar with infrared (IR) radiation and the IR spectrum, the frequencies of electromagnetic radiation generally characterized as infrared are emitted or absorbed by vibrating molecules, and such vibrations generally correspond to the thermal state of a material in relation to its surroundings. All solid bodies whose temperatures are above absolute zero radiate some infrared energy, and for temperatures up to about 3500K (3227° Celsius, 5840° Fahrenheit), such thermal radiation falls predominantly within the infrared portion of the electromagnetic spectrum. There thus exists a rather straightforward relationship between the temperature of a body and the infrared radiation which it emits. In the present invention, the monitoring of radiation in the range of 8-14 microns is currently preferred.

As further understood by those familiar with electromagnetic radiation, however, wavelengths below 2.5 microns (usually 0.8 to 2.5 microns or 4000-12,500 $cm^{-1}$) are also considered as the "near IR" portion of the electromagnetic spectrum, and represent vibrational "overtones" and low level electronic transitions. Similarly, wavelengths above 50 microns (usually 50 to about 1000 microns or 10-200 $cm^{-1}$) are considered to be the "far IR" portion of the electromagnetic spectrum and represent energy associated with molecular rotations.

It will thus be understood that the designation "infrared" is used in a descriptive rather than a limiting sense and that measurement of thermal radiation from eggs which falls outside of these particular frequencies is encompassed by the scope of the present invention.

Once the individual egg temperatures have been monitored, they are used to determine a comparative egg temperature for the selected group of eggs, it being understood that, as used herein, the term "comparative" means the computation of a relative standard temperature for the group against which the temperatures of the individual eggs can be compared, and which provides a threshold for determining whether any given egg is alive or dead.

Figure 1:
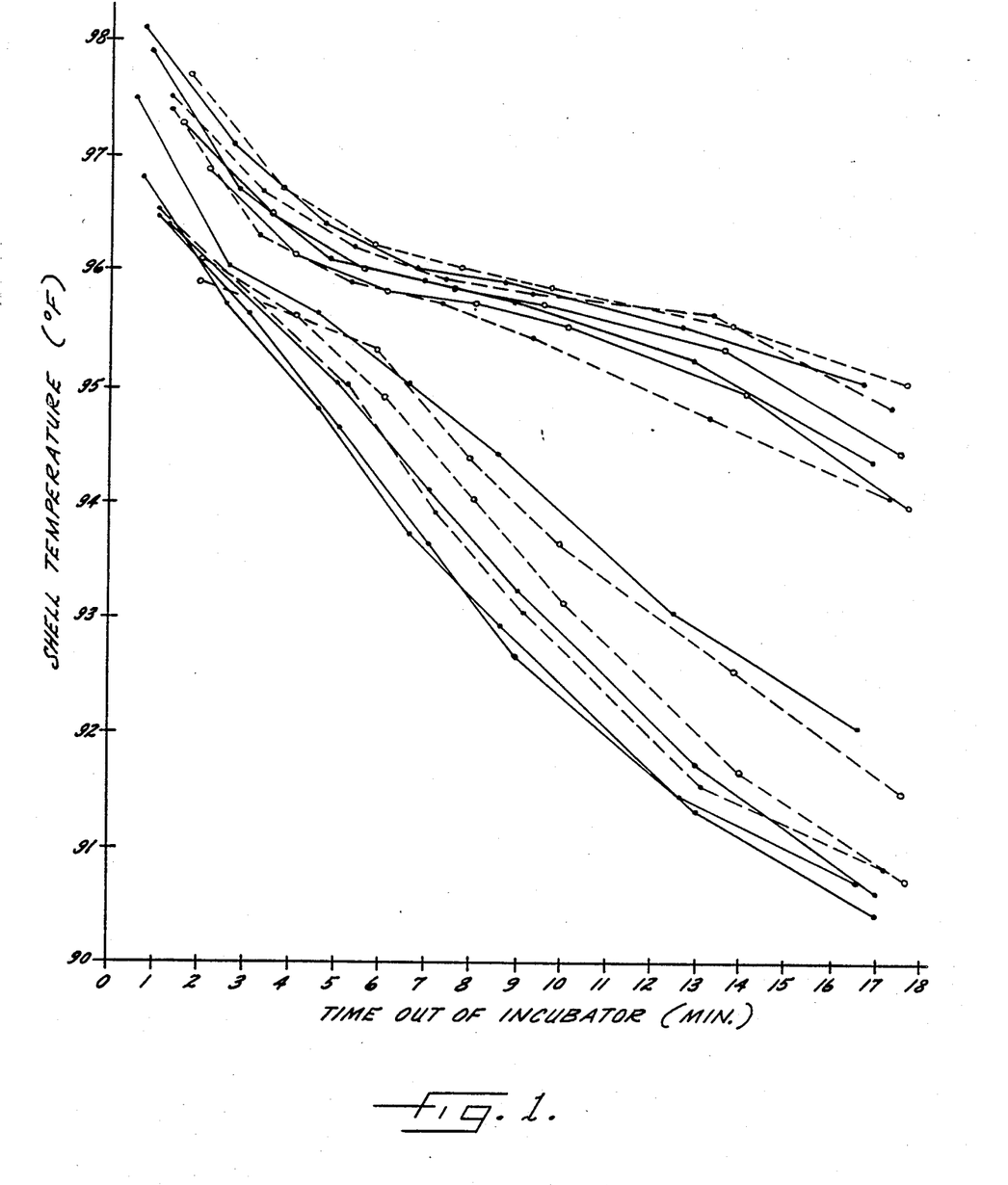
FIG. 1 is a graph of the shell temperature in degrees Fahrenheit of several eggs, both live and dead, plotted against the time period in minutes following the eggs' removal from an incubator.

FIG. 1 is a plot of the information set forth in Table I and shows actual temperatures of 21-day turkey eggs as measured by monitoring infrared radiation in the 8-14 micron wavelength range with a sensor located two inches from the bottom of individual eggs in a conventional 5 ×5 turkey flat. The temperature in the incubator is 99°, and the subsequent temperatures are recorded against the number of minutes that the eggs have been removed from the incubator. These temperatures illustrated in FIG. 1 were measured while the eggs were in a room having an air temperature of approximately 80° F. As indicated in FIG. 1, as the eggs cool, live eggs cool less rapidly than dead eggs, and the temperatures of the eggs following removal from the incubator demonstrate a distinct bi-modal distribution as they cool.

Figure 2:
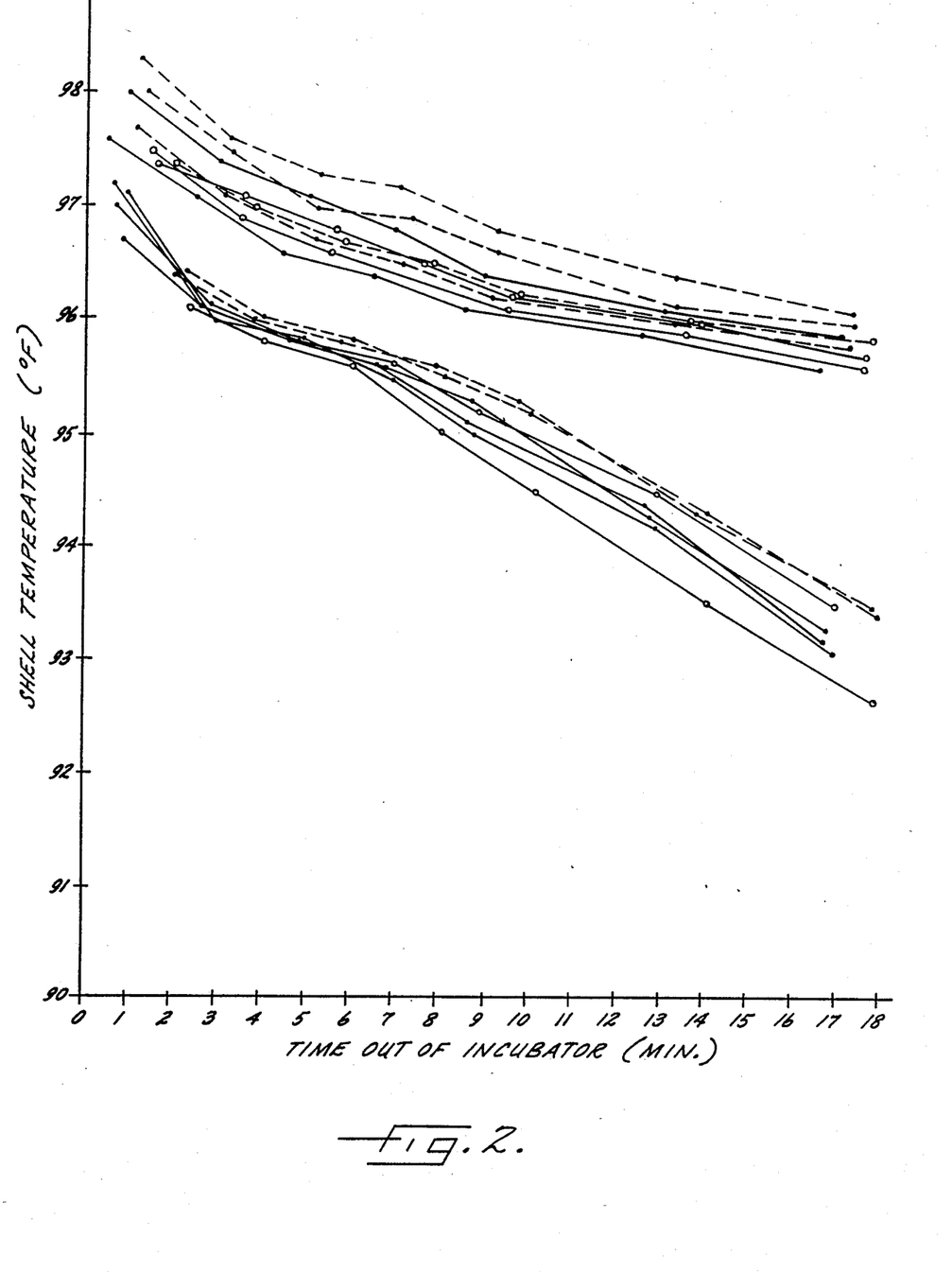
FIG. 2 is a graph similar to FIG. 1 reflecting second group of live and dead eggs.

FIG. 2 is a plot similar to that of FIG. 1 and illustrates graphically the information contained in Table II.

| | TIME | | | | | | | |
|---|---|---|---|---|---|---|---|---|
| Egg | (0:30) | (2:30) | (4:30) | (6:30) | (8:30) | (12:30) | (16:30) | (20:30) |
| 1 | 97.5 | 96.0 | 95.6 | 95.0 | 74.4 | 93.0 | 92.0 | 91.3 |
| 2 | 96.8 | 95.7 | 94.8 | 93.7 | 92.9 | 91.4 | 90.7 | 90.0 |
| 3 | 98.1 | 97.1 | 96.4 | 96.0 | 95.9 | 95.5 | 95.0 | 94.1 |
| 4 | 97.9 | 96.7 | 96.1 | 95.9 | 95.7 | 95.2 | 94.3 | 93.7 |
| 5 | 96.5 | 95.6 | 94.6 | 93.6 | 92.6 | 91.3 | 90.4 | 89.8 |
| 6 | 96.5 | 95.7 | 95.0 | 94.1 | 93.2 | 91.7 | 90.6 | 89.9 |
| 7 | 96.4 | 95.7 | 95.0 | 93.9 | 93.0 | 91.5 | 90.8 | 90.0 |
| 8 | 97.4 | 96.3 | 95.9 | 95.7 | 95.4 | 94.7 | 94.0 | 93.7 |
| 9 | 97.5 | 96.7 | 96.2 | 95.9 | 95.8 | 95.6 | 94.8 | 94.6 |
| 10 | 97.3 | 96.4 | 96.0 | 95.8 | 95.6 | 95.0 | 94.1 | 93.6 |
| 11 | 97.3 | 96.5 | 96.0 | 95.8 | 95.7 | 95.3 | 94.4 | 93.4 |
| 12 | 97.7 | 96.7 | 96.2 | 96.0 | 95.8 | 95.5 | 95.0 | 94.5 |
| 13 | 96.1 | 95.6 | 95.3 | 94.4 | 93.6 | 92.5 | 91.4 | 90.7 |
| 14 | 95.9 | 95.6 | 94.9 | 94.0 | 93.1 | 91.6 | 90.8 | 90.1 |

-continued

| 15 | 96.9 (2:07) | 96.1 (4:04) | 95.8 (6:10) | 95.8 (8:05) | 95.5 (10:08) | 94.9 (14:04) | 93.9 (18:03) | 93.2 (21:58) |

Pattern in Flat:

| 1 | 6 | 11 |
|---|---|----|
| 2 | 7 | 12 |
| 3 | 8 | 13 |
| 4 | 4 | 14 |
| 5 | 10 | 15 |

TABLE II

SETTER TEMP = 100° F.
Ambient IR = 89.1° F. Air Temp = 80.0° F.

| | TIME: | | | | | | | |
|---|---|---|---|---|---|---|---|---|
| | (0:30) | (2:30) | (4:30) | (6:30) | (8:30) | (12:30) | (16:30) | (20:30) |
| 1 | 97.6 | 97.1 | 96.6 | 96.4 | 96.1 | 95.9 | 95.6 | 95.0 |
| 2 | 97.2 | 96.1 | 95.8 | 95.6 | 95.1 | 94.4 | 93.2 | 92.4 |
| 3 | 97.0 | 96.1 | 95.8 | 95.6 | 95.3 | 94.3 | 93.3 | 92.5 |
| 4 | 97.1 | 96.0 | 95.8 | 95.5 | 95.0 | 94.2 | 93.1 | 92.3 |
| 5 | 96.7 | 96.0 | 95.5 | 95.6 | 95.2 | 94.5 | 93.5 | 92.6 |
| 6 | 98.0 | 97.4 | 97.1 | 96.8 | 96.4 | 96.1 | 95.9 | 95.6 |
| 7 | 97.7 | 97.1 | 96.7 | 96.5 | 96.2 | 96.0 | 95.8 | 95.6 |
| 8 | 98.3 | 97.6 | 97.3 | 97.2 | 96.8 | 96.4 | 96.1 | 95.9 |
| 9 | 98.0 | 97.5 | 97.0 | 96.9 | 96.6 | 96.1 | 96.0 | 95.8 |
| 10 | 97.5 | 96.9 | 96.6 | 96.2 | 96.1 | 95.9 | 95.6 | 95.3 |
| 11 | 97.4 | 97.1 | 96.8 | 96.5 | 96.2 | 96.0 | 95.7 | 95.3 |
| 12 | 96.4 | 96.0 | 95.8 | 95.6 | 95.3 | 94.3 | 93.5 | 92.6 |
| 13 | 97.4 | 97.0 | 96.7 | 96.5 | 96.2 | 96.0 | 95.9 | 95.6 |
| 14 | 96.4 | 96.0 | 95.8 | 95.5 | 95.2 | 94.3 | 93.4 | 92.7 |
| 15 | 96.1 | 95.8 | 95.6 | 95.0 | 94.5 | 93.5 | 92.6 | 91.7 |

Pattern in Flat:

| 1 | 6 | 11 |
|---|---|----|
| 2 | 7 | 12 |
| 3 | 8 | 13 |
| 4 | 9 | 14 |
| 5 | 10 | 15 |

In a commercial hatchery, turkey eggs are typically transferred from setting flats to hatching baskets at day 21 of the gestation period (such eggs typically hatch at around day 28). Typically, manual candling is performed during the transfer process, as in any in-ovo injection. Because flats of eggs are carried on carts with about 5,000 eggs to the cart, the specific time that any given egg or group of eggs will have been out of the incubator is generally unknown. Generally, hatcheries limit the time that the eggs spend out of the incubators to about 20 minutes or less.

Accordingly, because of the various unknowns, including the amount of time out of the incubator, differences in the temperature of the room air, the flow rate of room air, and variation in incubator temperatures, it is generally impossible to determine whether any given egg is alive or dead by measuring its temperature alone. The measurement of the individual temperatures of a group of eggs, however, allows the calculation of a comparative temperature based upon the range of temperatures, the distribution of temperatures, and the probability that a flat contains at least one or more dead eggs. With this information, the determination of whether any individual egg is live or dead becomes much more probable. FIG. 1 illustrates that even live eggs show significant scatter in their individual temperatures at any given time primarily due to differences in egg size and shape, the metabolism of the individual embryos, the egg's position in the flat, and the prior thermal history of the egg.

Therefore, the use of a comparative egg temperature rather than some absolute temperature standard offers a number of advantages. For example, dead turkey eggs cool at about twice the rate of live eggs or about 0.4° F. per minute. Therefore, after five minutes dead eggs are one to two degrees cooler than live eggs under identical thermal conditions. If the absolute temperature of a single egg was used to determine its individual status, however, the problem arises that both live and dead eggs cool rapidly after leaving an incubator so that the absolute temperatures of both live and dead eggs change constantly with time and cannot, standing alone, indicate the status of an individual egg. Furthermore, when measuring a group of eggs such as on a setting flat or tray, those eggs on the outside tend to cool slightly more rapidly than eggs in the center and eggs from different regions of an incubator vary in temperature as well.

In one embodiment, the comparative temperature can be calculated using statistical methods to optimally partition the distribution of alive and dead egg temperatures into a bimodal distribution of live egg temperatures and dead egg temperatures.

Once the individual temperatures have been monitored and the comparative egg temperature determined, the next step in the method of the invention is the determination of the difference between each individual egg temperature and the comparative egg temperature of the selected group, following which the resulting status of each egg may be determined. Dead eggs can be identified to a high degree of precision and accuracy on the basis of the difference between their monitored individual temperatures and the comparative egg temperature of the selected group.

In another embodiment, the method comprises calculating a mean and standard deviation for the warmest third of the eggs in any selected group. Choosing such a warmest fraction of the eggs greatly increases the probability that all of the eggs in that fraction are alive. The comparative temperature between live and dead eggs can then be calculated as being equal to the mean temperature less N standard deviations. The value of N is typically set at a value of between about 3 and about 5 depending upon the various environmental circumstances discussed earlier.

In yet another embodiment, the method comprises measuring the temperatures of all of the eggs twice with a 30-second interval between measurements. Because dead eggs cool about twice as rapidly as live eggs, the distribution of cooling rates for all of the eggs in any selected group will generally form a bimodal distribution, thereby facilitating identification of live and dead eggs. This method is particularly useful if the egg temperatures are to be monitored immediately after the eggs have been removed from a warm incubator. As indicated earlier, however, such monitoring immediately after exit from the incubator cannot always be accomplished, making the other embodiments of the invention useful in these other circumstances.

Once particular eggs are identified as dead, the method further comprises removing the eggs which are identified as dead from the selected group of eggs so that the necessity, expense and potential for contamination of any further handling of the dead eggs are eliminated.

Figure 3:
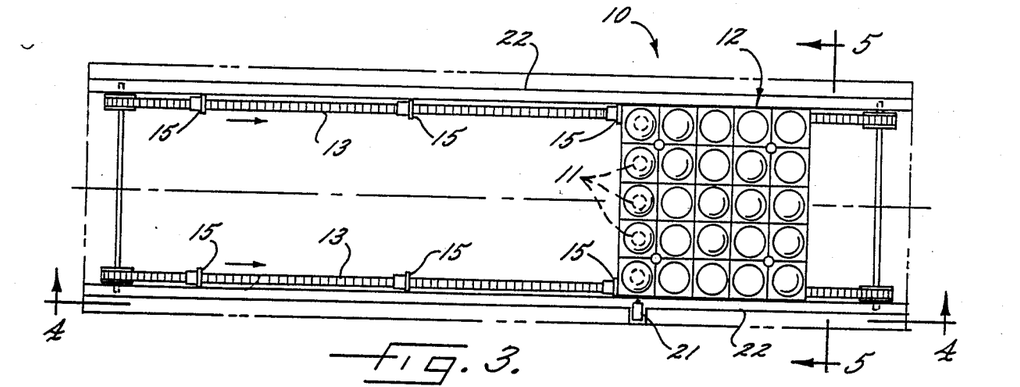
FIG. 3 is a plan view of an apparatus according to the present invention.
Figure 4:
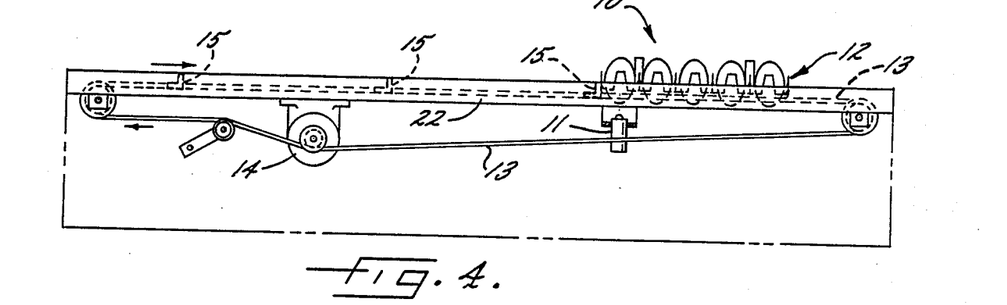
FIG. 4 is an elevational view taken along lines 4—4 of FIG. 3.
Figure 5:
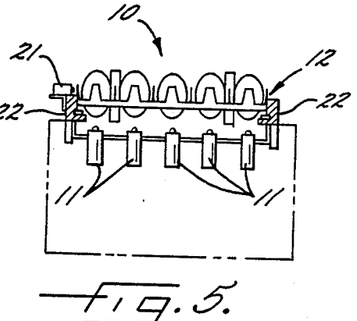
FIG. 5 is an elevational view taken along lines 5—5 of FIG. 3.

Further aspects of the method and appropriate apparatus are best described with respect to the drawings. FIGS. 3, 4 and 5 show a basic apparatus generally designated at 10 which can be used in accordance with the method of the present invention. Apparatus 10 includes a series of infrared radiation sensors 11, five of which are shown aligned in a row in the illustrated embodiment, and means for moving a fixed array of eggs to a predetermined aligned position on the apparatus 10 with respect to the infrared sensors 11. Other embodiments allow temperature measurements to be made by contact temperature sensors such as thermistors or thermocouples which are placed against the side or the bottom of eggs. FIG. 8 shows a contact based temperature sensor broadly designated at 25 in position against an egg in a portion of the flat 12.

Figure 6:
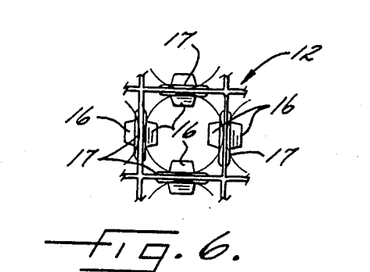
FIG. 6 is an enlarged view of one cell of a standard egg setting flat.
Figure 7:
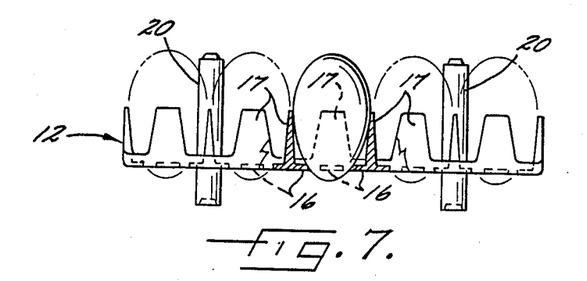

In the illustrated drawings, the fixed array of eggs comprises an open bottom setting flat 12 of eggs. The flat 12 carries 25 eggs in an array of five rows of five eggs each and rides on conveyor means which are shown in the form of drive chains 13, chain drive motor 14 and chain drive dogs 15. The open bottom setting flat is illustrated in greater detail in FIGS. 6 and 7. FIG. 6 is a plan view of a one egg unit portion of a standard open bottom setting flat showing the four bottom supports 16 and the four side supports 17 upon and within which an egg rests. Stacking poles 20 are also illustrated and are used in different contexts when flats of eggs are to be stacked upon one another. If desired, standard trays can be used as the fixed array of eggs. Such trays generally support four of the standard flats, thereby carrying a total of 100 eggs.

As illustrated in the drawings, the invention thus comprises moving a fixed array of eggs to a predetermined aligned position with respect to the infrared sensors 11. In a preferred embodiment, a photoreflective detector 21 is used in conjunction with the chain drive system to stop the open bottom flat 12 so that one row of eggs in the flat 12 is in a predetermined aligned position with respect to the infrared sensors 11. In this embodiment, each of the five respective eggs in the row is aligned with one of the five individual sensors 11 (FIG. 5). After the infrared radiation emitted by each egg in one such row has been monitored, it is converted to a temperature value, typically by using a standard algorithm and calibration data for each sensor. Alternatively, sensors which are referred to as "infrared thermometers" can be used which produce an output in degrees Celsius or Fahrenheit which require no further conversion. The temperature value of each egg is then recorded, with any appropriate memory device, but with a microprocessor-driven computer preferred. The next successive row of eggs in the flat 12 is moved to the predetermined aligned position in which that row is successively aligned with the infrared sensors 11, and the monitoring, converting and recording steps repeated.

Each row of eggs in the standard setting flat 12, or in a tray where appropriate, is advanced over the row of infrared sensors 11 after which the measuring, recording and advancing steps are repeated for each row of eggs until the infrared radiation from each egg has been measured and the temperature of each egg recorded. A threshold temperature is calculated, and eggs are identified as dead when their monitored and recorded temperatures are below the threshold temperature. For example, the threshold temperature may be calculated for which 70 percent of the eggs are cooler, and then dead eggs may be indentified as those whose measured temperatures are more than 1 degree Fahrenheit cooler than the threshold temperature.

The chain drive typically moves the flats continuously at a speed of about one inch per second along the guide rails 22 adjacent the path of the chain 13. Faster speeds are, however, possible using infrared sensors of quicker response time or incremental motion. The output of each of the sensors can be amplified and fed to a computer through an analog to digital converter. Conversion of the signals occurs in a very short period of time, typically less than one millisecond, and as the response time of the infrared sensors is on the order of about 0.5 seconds, the speed of the chain drive is more than moderate enough to allow all of the calculations and measurements to take place.

Using the computer and an appropriate algorithm, the comparative egg temperature of 25 eggs in a flat or 100 eggs in a tray can be quickly determined. The computer then compares the recorded temperature of each individual egg to the threshold egg temperature and identifies those eggs whose temperatures differ from the comparative egg temperature. The eggs identified as dead can be removed by any conventional method, including suction-type lifting devices as are disclosed in U.S. Pat. No. 4,681,063, the contents of which are incorporated herein by reference.

Therefore, the method of the invention inherently corrects for any cooling of the eggs prior to measurement, for differences in the temperatures of individual eggs, whether due to position on the fixed array, position in an incubator, or rate of cooling under the given thermal conditions.

If the mean temperatures of a row of eggs is more than 1 or 2 degrees above or below the mean temperature of other rows, the infrared sensor for that row may be dirty or may have failed to perform properly. In the preferred embodiment of the invention, temperatures more than about 3° warmer or about 6° cooler than the mean temperature or threshold temperature are used to identify malfunctioning sensors. The computer can accordingly be programmed to identify such sensors on the basis of such measurements and to signal an operator appropriately.

In the drawings and specification, there have been typical preferred embodiments of the invention and, although specific terms are employed, they are used in a generic and descriptive sense only and not for purposes of limitation, the scope of the invention being set forth in the following claims.

That which is claimed is:

1. A method of distinguishing between live and dead poultry eggs, the method comprising:
   (a) monitoring the individual temperatures of a selected group of eggs;
   (b) using the monitored individual egg temperatures to determine a comparative egg temperature for the selected group of eggs;
   (c) determining the difference between each individual egg temperature and the comparative egg temperature of the selected group; and
   (d) identifying eggs as live or dead on the basis of the difference between their monitored individual temperatures and the comparative egg temperature of the selected group.

2. A method according to claim 1 wherein the step of monitoring the individual temperatures comprises monitoring the infrared radiation emitted from the individual eggs in the selected group.

3. A method according to claim 2 further comprising converting the monitored infrared radiation from each individual egg to a temperature value for each individual egg.

4. A method according to claim 2 wherein the step of monitoring the infrared radiation comprises monitoring the infrared radiation emitted from the egg at the non-air cell end of the egg.

5. A method according to claim 1 wherein the step of monitoring the individual temperatures comprises monitoring the individual temperatures by placing a contact based temperature sensor against the individual eggs.

6. A method according to claim 1 wherein the step of determining a comparative egg temperature for the selected group comprises determining the mean temperature of the selected group of eggs.

7. A method according to claim 1 wherein the step of determining the comparative egg temperature of the selected group of eggs comprises identifying a threshold temperature for which a predetermined percentage of eggs in the selected group are either cooler or warmer than the threshold temperature.

8. A method according to claim 1 further comprising removing eggs identified as dead from the selected group of eggs.

9. A method of using infrared radiation to distinguish between live and dead poultry eggs, the method comprising:
   moving a fixed array of eggs to a predetermined aligned position with respect to an infrared sensor;
   measuring the infrared radiation emitted by each egg in the fixed array of eggs;
   calculating a threshold temperature for which 70 percent of the eggs measured in the fixed array are cooler;
   identifying as dead eggs in the fixed array whose measured temperatures were more than 1 degree Fahrenheit cooler than the threshold temperature; and
   removing the eggs identified as dead from the fixed array of eggs.

10. A method according to claim 9 wherein the step of moving a fixed array of eggs comprises aligning the fixed array of eggs with an array of infrared sensors so that each respective egg is aligned with an individual sensor.

11. A method according to claim 10 further comprising:
   identifying eggs in the array for which the individual sensors monitor temperatures which are either about 3 or more degrees Fahrenheit warmer than the threshold temperature or about 6 or more degrees Fahrenheit cooler than the threshold temperature; and
   identifying as malfunctioning the individual sensors which monitor the identified eggs.

12. A method according to claim 9 wherein the step of moving a fixed array of eggs comprises moving a row of eggs to a predetermined aligned position in which the row of eggs in the flat is aligned with an infrared sensor.

13. A method according to claim 12 wherein the step of aligning the row of eggs with an infrared sensor comprises aligning the row of eggs with a row of infrared sensors so that each respective egg is aligned with an individual sensor.

14. A method according to claim 12 wherein the step of moving a fixed array of eggs comprises moving successive rows of eggs to a predetermined aligned position in which each row is successively aligned with an infrared sensor.

15. A method of using infrared radiation to distinguish between live and dead poultry eggs, the method comprising:
   (a) moving an open bottom flat of eggs to an aligned position in which one row of eggs in the flat is aligned over a row of infrared sensors with each sensor being aligned with a single egg in the row;
   (b) measuring the infrared radiation emitted by each egg through the open spaces in the bottom of the standard setting flats;
   (c) recording the temperature of each egg in the row;
   (d) advancing a next row of eggs in the standard setting flat over the row of infrared sensors;
   (e) repeating steps (b), (c) and (d) for each row of eggs in the standard setting flat until the infrared radiation from each egg has been measured and the temperature of each egg recorded;
   (f) calculating a threshold temperature for which 70 percent of the eggs measured in the standard setting flat are cooler;
   (g) identifying as dead eggs in the standard setting flats whose recorded temperatures were more than 1 degree Fahrenheit below the threshold temperature; and
   (h) removing the eggs identified as dead from the standard setting flat.

16. A method of distinguishing between live and dead poultry eggs, the method comprising:
   (a) monitoring the individual temperatures of a selected group of eggs;
   (b) statistically organizing the temperatures into a bimodal distribution;
   (c) identifying eggs as live or dead on the basis of the difference between their individual monitored temperatures and the mean temperatures of the bimodal distribution.

17. A method of distinguishing between live and dead poultry eggs, the method comprising:
(a) monitoring the individual temperatures of a selected group of eggs;
(b) identifying a predetermined fraction of the selected group of eggs as the warmest eggs of the selected group;
(c) calculating the mean temperature for the eggs in the predetermined fraction; and
(d) identifying individual eggs as live or dead on the basis of the difference between each individual egg temperature and the mean temperature of the predetermined fraction.

18. A method according to claim 17 further comprising calculating the standard deviation from the mean temperature and wherein the step of identifying individual eggs as live or dead comprises identifying eggs on the basis of the number of standard deviations away from the mean temperature that the individual egg temperature falls.

19. A method according to claim 18 wherein dead eggs are identified as falling between about 3 and about 5 standard deviations away from the mean temperature.

20. A method according to claim 17 wherein the step of identifying a predetermined fraction of the selected group of eggs comprises identifying the warmest one-third of the eggs in the selected group.

21. A method of distinguishing between live and dead poultry eggs, the method comprising:
(a) monitoring the initial individual temperatures of a selected group of eggs following their removal from an incubator and before the eggs reach an equilibrium with the ambient temperature;
(b) monitoring subsequent the individual temperatures of the same selected group of eggs at a selected interval of time following the monitoring of their initial temperatures;
(c) using the initial monitored temperatures and the subsequent monitored temperatures to determine the rate of cooling of each individual egg and a comparative rate of cooling for the selected group of eggs;
(d) determining the difference between the rate of cooling of each individual egg and the comparative rate of cooling for the selected group; and
(e) identifying eggs as live or dead on the basis of the difference between their individual rate of cooling and the comparative rate of cooling for the selected group.

* * * * *

UNITED STATES PATENT AND TRADEMARK OFFICE
CERTIFICATE OF CORRECTION

PATENT NO. : 4,914,672
DATED : April 3, 1990
INVENTOR(S) : John H. Hebrank

It is certified that error appears in the above-identified patent and that said Letters Patent is hereby corrected as shown below:

Column 3, Line 9, before "second", please insert --a--.

Column 3, Line 35, before "end", please insert --cell--.

Column 3, Line 46, "$cm^{-1}$" should be --$(cm^{-1}$--.

Signed and Sealed this

Fifteenth Day of October, 1991

Attest:

HARRY F. MANBECK, JR.

Attesting Officer    Commissioner of Patents and Trademarks